(12) United States Patent
Eveland et al.

(10) Patent No.: US 6,664,893 B1
(45) Date of Patent: Dec. 16, 2003

(54) METHOD FOR CONTROLLING ACCESS TO MEDICAL MONITORING DEVICE SERVICE

(75) Inventors: Doug C. Eveland, Carlsbad, CA (US); William R. Marable, Carlsbad, CA (US); Bobby E. Rogers, San Diego, CA (US)

(73) Assignee: CardioNet, Inc., San Diego, CA (US)

( * ) Notice: Subject to any disclaimer, the term of this patent is extended or adjusted under 35 U.S.C. 154(b) by 129 days.

(21) Appl. No.: 09/841,154

(22) Filed: Apr. 23, 2001

(51) Int. Cl.$^7$ .................................................. G08B 1/08
(52) U.S. Cl. .................... 340/539.12; 128/903; 340/5.8; 340/573.1; 455/411; 705/2
(58) Field of Search ............................... 340/573.1, 539, 340/531, 5.2, 5.8, 539.11, 539.12; 705/2, 3, 4; 379/38; 455/404.1, 410, 411; 607/60; 128/903, 904

(56) References Cited

U.S. PATENT DOCUMENTS

| | | | | |
|---|---|---|---|---|
| 3,478,344 | A | 11/1969 | Schwitzgebel et al. | 340/7.63 |
| 3,768,014 | A | 10/1973 | Smith et al. | 324/158.1 |
| 3,885,552 | A | 5/1975 | Kennedy | 607/27 |
| 3,902,478 | A | 9/1975 | Konopasek et al. | 600/519 |
| 3,925,762 | A | 12/1975 | Keitlinger et al. | 340/870.09 |
| 4,173,971 | A | 11/1979 | Karz | 128/702 |
| 4,183,354 | A | 1/1980 | Sibley et al. | 128/711 |
| 4,211,237 | A | 7/1980 | Nagel | 128/698 |
| 4,230,127 | A | 10/1980 | Larson | 128/706 |
| 4,241,237 | A | 12/1980 | Paraskevakos et al. | 379/106.06 |
| 4,457,315 | A | 7/1984 | Bennish | 128/704 |
| 4,531,527 | A | 7/1985 | Reinhold, Jr. et al. | 128/696 |
| 4,535,783 | A | 8/1985 | Marangoni | 128/711 |
| 4,598,272 | A | 7/1986 | Cox | 340/539 |
| 4,651,157 | A | 3/1987 | Gray et al. | 342/457 |
| 4,675,656 | A | 6/1987 | Narcisse | 340/539 |
| 4,706,689 | A | 11/1987 | Man | 600/302 |
| 4,742,357 | A | 5/1988 | Rackley | 342/457 |
| 4,750,197 | A | 6/1988 | Denekamp et al. | 455/404.2 |
| 4,777,478 | A | 10/1988 | Hirsch et al. | 340/573 |
| 4,785,291 | A | 11/1988 | Hawthorne | 340/573 |
| 4,819,860 | A | 4/1989 | Hargrove et al. | 228/668 |

(List continued on next page.)

FOREIGN PATENT DOCUMENTS

| | | |
|---|---|---|
| DE | 4414 907 | 6/1995 |
| EP | 0 834 846 | 1/1986 |
| EP | 0 484 880 | 11/1991 |
| EP | 0 811 959 | 6/1997 |
| EP | 1 072 994 | 1/2001 |
| FR | 2 787 905 | 12/1998 |
| WO | 94/13197 | 6/1994 |
| WO | WO 96 25877 | 8/1996 |
| WO | 97/00708 | 1/1997 |
| WO | WO 99 44494 | 9/1999 |
| WO | WO 00 30529 | 6/2000 |
| WO | WO 00 62663 | 10/2000 |

*Primary Examiner*—Thomas Mullen
(74) *Attorney, Agent, or Firm*—Fish & Richardson P.C.

(57) ABSTRACT

Access to medical monitoring device service is controlled by inputting a set of identification data elements into a medical monitoring device system, which then establishes a communication link with a central unit and communicating the set of identification data elements to the central unit. The medical monitoring device system and the central unit cooperatively determining whether the medical monitoring device may be activated for rendering medical monitoring device service, by evaluating the set of identification data elements as to whether they meet a set of basic structural requirements, and obtaining financial or other authorization from a third-party source. In the event that the identification data elements meet the set of basic structural requirements and the authorization is obtained, the central, unit issues an activation signal to the medical monitoring device system over the communication link.

19 Claims, 2 Drawing Sheets

U.S. PATENT DOCUMENTS

| | | | |
|---|---|---|---|
| 4,952,928 A | 8/1990 | Carroll et al. | 340/10.41 |
| 5,003,984 A | 4/1991 | Muraki et al. | 128/710 |
| 5,113,869 A | 5/1992 | Nappholz et al. | 128/696 |
| 5,172,698 A | 12/1992 | Stanko | 128/697 |
| 5,223,844 A | 6/1993 | Mansell et al. | 342/357 |
| 5,301,105 A * | 4/1994 | Cummings, Jr. | 705/2 |
| 5,309,920 A | 5/1994 | Gallant et al. | 128/710 |
| 5,311,197 A | 5/1994 | Sorden et al. | 342/457 |
| 5,318,592 A | 6/1994 | Schaldach | 607/5 |
| 5,321,618 A | 6/1994 | Gessman | 607/5 |
| 5,334,974 A | 8/1994 | Simms et al. | 340/990 |
| 5,335,664 A | 8/1994 | Nagashima | 128/696 |
| 5,336,245 A | 8/1994 | Adams et al. | 607/32 |
| 5,348,008 A | 9/1994 | Bornn et al. | 128/642 |
| 5,389,934 A | 2/1995 | Kass | 342/357 |
| 5,394,879 A | 3/1995 | Gorman | 128/707 |
| 5,418,537 A | 5/1995 | Bird | 342/356 |
| 5,422,816 A | 6/1995 | Sprague et al. | 455/556.2 |
| 5,423,869 A | 6/1995 | Poore | 607/18 |
| 5,458,123 A | 10/1995 | Unger | 128/696 |
| 5,461,365 A | 10/1995 | Schlager et al. | 340/573.4 |
| 5,470,233 A | 11/1995 | Fruchterman et al. | 434/112 |
| 5,479,482 A | 12/1995 | Grimes | 455/556.1 |
| 5,487,755 A | 1/1996 | Snell et al. | 607/27 |
| 5,497,149 A | 3/1996 | Fast | 340/988 |
| 5,503,158 A | 4/1996 | Coppock et al. | 128/696 |
| 5,504,491 A | 4/1996 | Chapman | 342/357 |
| 5,515,419 A | 5/1996 | Sheffer | 455/456.5 |
| 5,522,396 A | 6/1996 | Langer et al. | 128/696 |
| 5,544,661 A | 8/1996 | Davis et al. | 128/700 |
| 5,549,113 A | 8/1996 | Halleck et al. | 128/671 |
| 5,564,429 A | 10/1996 | Bornn et al. | 128/696 |
| 5,568,814 A | 10/1996 | Gallant et al. | 128/672 |
| 5,573,506 A | 11/1996 | Vasko | 604/65 |
| 5,576,952 A | 11/1996 | Stutman et al. | 600/300 |
| 5,579,775 A | 12/1996 | Dempsey et al. | 128/670 |
| 5,617,871 A | 4/1997 | Burrows | 128/696 |
| 5,620,472 A | 4/1997 | Rahbari | 607/27 |
| 5,626,624 A | 5/1997 | Schaldach et al. | 607/24 |
| 5,626,630 A | 5/1997 | Markowitz et al. | 607/60 |
| 5,629,678 A | 5/1997 | Gargano et al. | 340/573.4 |
| 5,649,303 A | 7/1997 | Hess et al. | 455/63 |
| 5,652,570 A | 7/1997 | Lepkofker | 340/573.4 |
| 5,678,562 A | 10/1997 | Sellers | 128/710 |
| 5,704,351 A | 1/1998 | Mortara et al. | 128/630 |
| 5,704,364 A | 1/1998 | Saltzstein et al. | 128/696 |
| 5,704,366 A | 1/1998 | Tacklind et al. | 128/716 |
| 5,713,856 A | 2/1998 | Eggers et al. | 604/65 |
| 5,720,770 A | 2/1998 | Nappholz et al. | 607/30 |
| 5,720,771 A | 2/1998 | Snell | 607/60 |
| 5,724,025 A | 3/1998 | Tavori | 340/573.1 |
| 5,729,197 A | 3/1998 | Cash | 340/539.3 |
| 5,730,143 A | 3/1998 | Schwarzberg | 128/710 |
| 5,731,757 A | 3/1998 | Layson, Jr. | 340/573.1 |
| 5,748,103 A | 5/1998 | Flach et al. | 340/870.07 |
| 5,749,367 A | 5/1998 | Gamlyn et al. | 128/696 |
| 5,749,907 A | 5/1998 | Mann | 607/27 |
| 5,752,976 A | 5/1998 | Duffin et al. | 607/32 |
| 5,759,199 A | 6/1998 | Snell et al. | 607/60 |
| 5,882,300 A | 3/1999 | Malinouskas et al. | 600/300 |
| 5,891,169 A | 4/1999 | Boheim et al. | 607/4 |
| 5,913,827 A | 6/1999 | Gorman | 600/509 |
| 5,913,881 A | 6/1999 | Benz et al. | 607/36 |
| 5,931,791 A | 8/1999 | Saltzstein et al. | 600/513 |
| 5,941,829 A | 8/1999 | Saltzstein et al. | 600/509 |
| 5,944,659 A | 8/1999 | Flach et al. | 600/300 |
| 5,950,110 A | 9/1999 | Hendrickson | 455/1 |
| 5,959,529 A | 9/1999 | Kail, IV | 340/539 |
| 5,964,794 A | 10/1999 | Bolz et al. | 607/121 |
| 5,966,692 A | 10/1999 | Langer et al. | 705/3 |
| 5,970,986 A | 10/1999 | Bolz et al. | 128/899 |
| 5,987,352 A | 11/1999 | Klein et al. | 600/509 |
| 5,987,519 A | 11/1999 | Peifer et al. | 709/230 |
| 6,026,008 A | 2/2000 | Feese | 365/63 |
| 6,038,469 A | 3/2000 | Karlsson et al. | 600/512 |
| 6,073,046 A | 6/2000 | Patel et al. | 600/509 |
| 6,083,248 A | 7/2000 | Thompson | 607/30 |
| 6,088,608 A | 7/2000 | Schulman et al. | 600/345 |
| 6,093,146 A | 7/2000 | Filangeri | 600/300 |
| 6,101,478 A * | 8/2000 | Brown | 705/2 |
| 6,102,856 A | 8/2000 | Groff et al. | 600/301 |
| 6,154,674 A | 11/2000 | Meier | 607/22 |
| 6,160,478 A | 12/2000 | Jacobsen | 340/539.12 |
| 6,181,966 B1 | 1/2001 | Nigram | 607/4 |
| 6,192,274 B1 | 2/2001 | Worzewski | 607/14 |
| 6,225,901 B1 | 5/2001 | Kail, IV | 340/539.11 |
| 6,245,092 B1 | 6/2001 | Schaldach | 607/1 |
| 6,263,243 B1 | 7/2001 | Lang | 607/17 |
| 6,466,793 B1 | 10/2002 | Wallstedt et al. | 455/450 |
| 2002/0143576 A1 * | 10/2002 | Nolvak et al | 705/2 |

* cited by examiner

METHOD FOR CONTROLLING ACCESS TO MEDICAL MONITORING DEVICE SERVICE

This invention relates to the rendering of medical monitoring device service and, more particularly, to ensuring that access to such service is authorized prior to commencing the service.

BACKGROUND OF THE INVENTION

Advances in sensor technology, electronics, and communications have made it possible for physiological characteristics of patients to be monitored even when the patients are ambulatory and not in continuous, direct contact with a hospital monitoring system. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient according to the medical problem of the patient, such as the heartbeat and its waveform.

One of the business problems associated with the use of such medical monitoring devices is establishing whether the patient's health-care-benefit payer has authorized the use of the monitoring device and service. In the absence of a proper authorization, the patient may use the medical monitoring device and incur significant charges in the form of rental value of the medical monitoring device, telephone charges, charges at the central monitoring system, and charges by medical personnel, and the providers of those goods and services may not get paid. Bad debts are a continuing concern in the medical field generally. Bad debts are of even greater concern in the case of a portable medical monitoring device and its service where the physical control of the device is in the hands of a third party, such as a prescribing doctor, who does not own the medical monitoring device and is not responsible for improper charges.

There is a need for an approach to controlling access to such medical monitoring devices and their services to ensure that only a properly authorized patient can obtain the service. The present invention fulfills this need, and further provides related advantages.

SUMMARY OF THE INVENTION

The present invention provides a method for controlling access to medical monitoring devices and service. The approach ensures that service is initiated and continued only for persons who are properly authorized to have the service. The present approach activates the medical monitoring device and its service only for a person who provides proper identification data and is financially and otherwise properly authorized for the service. The chances of the wrong person being monitored are also reduced. The activation process is quick and largely transparent to the person seeking the service, other than the requirement for inputting the proper identification data.

In accordance with the invention, a method for controlling access to medical monitoring device service comprises the steps of providing a medical monitoring device system having communications access to a central unit, inputting a set of identification data elements into the medical monitoring device system, the medical monitoring device system establishing a communication link with the central unit and communicating the set of identification data elements to the central unit, and the medical monitoring device system and the central unit cooperatively determining whether the medical monitoring device may be activated for rendering medical monitoring device service. The step of determining includes the steps of evaluating the set of identification data elements as to whether they meet a set of basic structural requirements, and obtaining authorization from a third-party source, which evaluating and obtaining steps are preferably done automatically. These evaluating and obtaining steps are typically performed by the central unit, but they may be distributed. In the event that the identification data elements meet the set of basic structural requirements and authorization is obtained, an activation signal is issued to the medical monitoring device system over the communication link. Third-party authorization sources include, for example, an insurance company, the social security administration, a credit-granting company, a physician, and a company responsible for the proper functioning of the medical monitoring device.

In an application of particular interest, the medical monitoring device system comprises a patient-portable unit. It may also include a base station that communicates with the patient-portable unit and also communicates with the central unit. The base station receives the identification data element input and communicates that information with the patient-portable unit and with the central unit as necessary by a land-line or a wireless communication link, as appropriate. The medical monitoring device system may aid the person seeking to gain access to service by locally performing a preliminary evaluation of the set of identification data elements as to whether they meet a set of format requirements, and providing an input diagnostic message in the event that the step of performing a preliminary evaluation determines that the set of identification data elements does not meet the set of format requirements. Such identification data elements may include, for example, a patient name, a patient address, a patient social security number, a patient sex, an identification of the third-party financial source, payment codes, and the name of the patient's physician.

The activation signal may serve only to activate the medical monitoring device and its services, or the activation signal may serve as an identifier that is included in all subsequent communications between the medical monitoring device and the central unit.

The present approach ensures that medical monitoring device services are provided to properly identified and authorized persons. It also ensures that all persons and agencies responsible for the medical monitoring device and the services are coordinated in their approval of rendering service to the particular patient and in effect have "signed off" on the provision of service and the type of service to be provided. Potential legal and financial liability is thereby reduced. Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
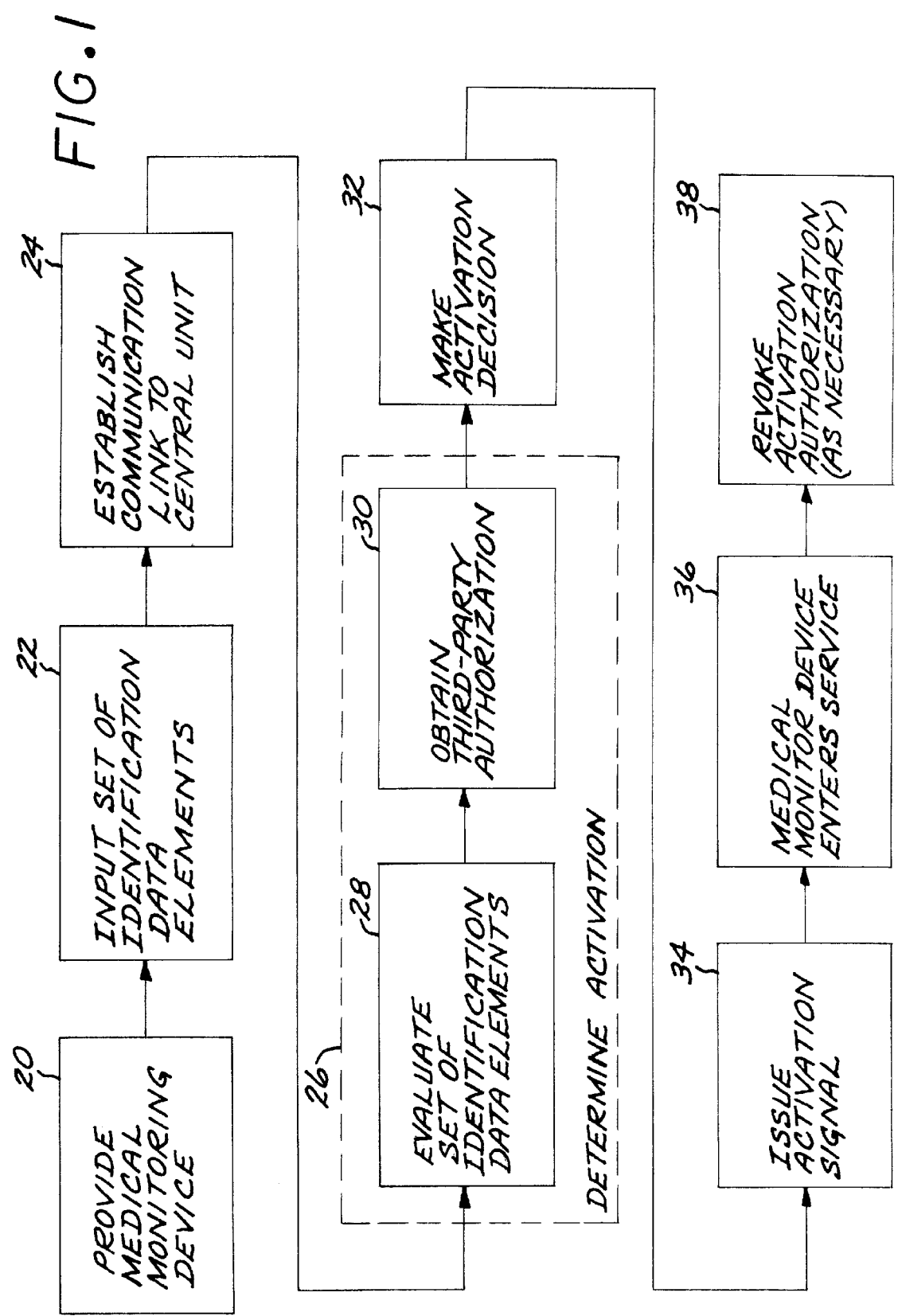
FIG. 1 is a block flow diagram of a preferred approach for practicing the invention.

FIG. 1 depicts a preferred approach for practicing the method of the invention for controlling access to medical monitoring device service. A medical monitoring device and its associated system are provided, numeral 20. The medical monitoring device and medical monitoring system may be of any operable type, such as that disclosed in U.S. Pat. No. 5,959,529, whose disclosure is incorporated in its entirety, and modified as discussed herein.

Figure 2:
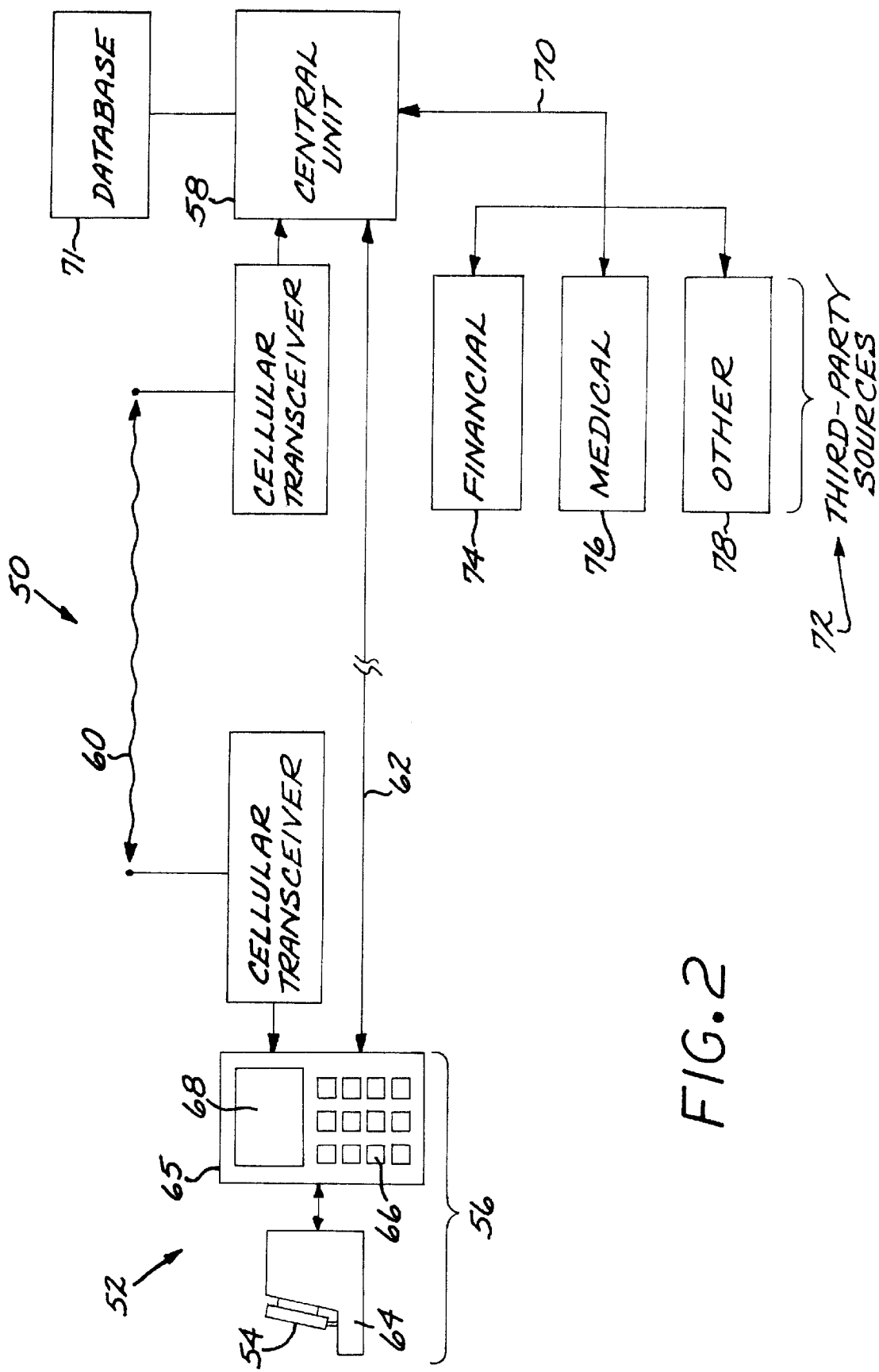
FIG. 2 is a schematic illustration of a system for implementing the preferred approach of FIG. 1.

FIG. 2 depicts the portions of a preferred form of a medical monitoring system 50 that are pertinent to the present invention. The medical monitoring system 50 includes a medical monitoring device system 52, which in turn comprises the medical monitoring device 54 and a base station 56. The medical monitoring device 54 is preferably a portable or remote monitoring unit of the type generally described in the '529 patent. The base station 56 has communication access to a central unit 58 through a communication link such as a wireless cellular telephone transceiver link 60 and/or a telephone land-line 62. In this embodiment, the base station 56 has a base station cradle 64 that receives the medical monitoring device 54 therein and establishes communication between the medical monitoring device 54 and an input/output device 65 that typically includes a microprocessor, communications controller, and communications hardware to establish the links 60 and/or 62. The input/output device 65 has a keypad 66 for inputting information and a display 68 to view the input information and other information to be displayed, as well as information transmitted to the input/output device 65.

The central unit 58 has communications access to a variety of databases 71 and to third-party sources 72, typically by telephone land-line 70. The databases 71 may include prior patient records, general records, and the like. The third-party sources 72 may include, for example, financial sources 74, medical sources 76, and other sources 78. A financial source might be, for example, an insurance company, the social-security administration, or a credit-granting company. A medical source might be, for example, a specialist physician whose authorization is required before commencing the monitoring of the patient. Other third-party sources might be, for example, the company that maintains the medical monitoring device 54 and which is consulted to be certain that the specific medical monitoring device to be activated is approved for service.

The base station 56 ordinarily resides in the office of the agency that is providing the medical monitoring device 54 to a patient for the purpose of monitoring physiological parameters of the patient. Such an agency could be, for example, the patient's physician or a hospital. When the agency undertakes to provide the medical monitoring device 54 to the patient, the medical monitoring device 54 is docked with the base station 56, and the procedures described in relation to subsequent portions of FIG. 1 are followed.

Returning to FIG. 1, a set of identification data elements are input into the medical monitoring device system 52, numeral 22, through the keypad 66 of the input/output device 65 of the base station 56 in the system 50 of FIG. 2. The identification data elements may include, for example, a patient name, a patient address, a patient social security number, a patient sex, and an identification of the third-party financial source. The identifier of the medical monitoring device 54, such as its serial number, may be manually input in step 22, but more normally the identifier is automatically made available by the medical monitoring device 54 to the base station 56.

The base station 56 may perform a preliminary evaluation of the set of identification data elements as to whether they meet a set of format requirements using software utility programs. Such basic format requirements are specified for each of the identification data elements. For example, a patient name should include only alphanumeric characters. If as typed into the keyboard the patient name includes other characters (e.g., a percent sign %), the base station recognizes the error and provides an input diagnostic message through the display 68 to prompt the input of correct information. In another example, a social security number must contain 10 numerical digits, and may not contain letters or other characters.

After what appears from the preliminary format evaluation to be a set of correct identification data elements is input to the medical monitoring device system 52, the medical monitoring device system 52 establishes a communication link, numeral 24, to the central unit 58. The communication link is preferably through the land-line 62, but may be through the cellular telephone transmission link 60 if the land-line is not available.

The medical monitoring device system 52 and the central unit 58 cooperatively determine whether the medical monitoring device 54 may be activated for rendering medical monitoring device service, numeral 26. The final decision is typically made by the central unit 58, although the medical monitoring device system 52 may aid in data processing or may be called upon for additional input, such as where the patient name is found not to match with the social security number in other records.

The step 26 of determining includes the steps of evaluating the set of identification data elements as to whether they meet a set of basic structural requirements, numeral 28, and obtaining third-party authorization from one or more of the third-party sources 72, numeral 30. The steps of evaluating 28 and obtaining 30 are preferably performed automatically. "Automatically" means herein that the steps are performed without human action or intervention, except where a discrepancy occurs. The present system is organized to perform the evaluating and obtaining steps entirely by computer procedures, to minimize costs and take advantage of data collections at a variety of locations. The present approach may be performed using manual (i.e., human-performed) steps 28 and 30, but that is less desirable.

The set of basic structural requirements that must be met may include the format requirements evaluated by the base station 56, but may also include other structural requirements. For example, the central unit may check the database 71 to attempt to match the input patient name with a social security number that is already in the database 71 from prior medical contacts. If the patient name and the social security number that were input in step 22 do not match, then further inquiry may be made back to the medical monitoring device system 52. The failure to match the name and the social security number may arise from a simple inputting error, which can be corrected with revised input, or it may arise from a fraudulent attempt to obtain medical monitoring services that is detected by the procedures of step 28.

The obtaining of third-party authorization in step 30 includes contacting appropriate third-party sources 72. The financial source 74 may be contacted to determine whether it authorizes the charges associated with the patient monitoring services. This authorization is particularly important for the business interests of the provider of the services, to avoid unpaid billings. Unpaid billings for medical services represents a major loss for many medical service companies. The medical source 76 may be contacted to determine whether it authorizes the patient monitoring. For example, if the prospective patient is being treated by more than one physician, it may be important to obtain authorization from each physician who is treating the patient before medical monitoring services are commenced. In this case, "authorization" signals form recognition by the authorizing party that monitoring information will be available. Other sources 78 may also be contacted to determine whether they authorize the patient monitoring. For example, it may be desirable to ensure that the company responsible for maintaining the specific medical monitoring device 54 that is to be activated authorizes its use. If a prior user had reported a problem and the specific medical monitoring device 54 had been taken out of service for repair, but was mistakenly to be re-activated without being repaired, the company responsible for the maintenance could prevent its activation at this stage.

Thus, the procedures in step 26 act as a "sign off" by a number of checks and third-parties to minimize the possibility that a medical monitoring device will be wrongly issued to a patient and activated. If the sign-offs are not completed, the medical monitoring device is not activated until the reason for the non-completion may be investigated. It is expected that in the great majority of cases, the activation determination of step 26 will be completed without incident and so rapidly that the checking will be transparent to the patient and the issuer of the medical monitoring device.

The activation decision is made, numeral 32. The final decision is typically made at the central unit 58. The decision is made at the central unit 58 because it has the access to the required information in step 26, and because it is more immune to tampering than is the base station 56.

In the event that the identification data elements meet the set of basic structural requirements and third-party authorization is obtained, the central unit 58 issues an activation signal to the medical monitoring device system 52 over the communication link 60 or 62, numeral 34. The medical monitoring device 54 is activated and enters service, numeral 36.

The "activation signal" may be of any operable type. It may be as simple as a software "on" switch that enables the processing of data within a microprocessor in the medical monitoring device 54 or a hardware "on" switch that turns on particular hardware functions such as the communications links built into the medical monitoring device 54. The activation signal may be more complex, and may include identification of the patient and the specific medical monitoring device 54 that is associated with that patient. This activation signal may then be transmitted with each subsequent communication between the medical monitoring device 54 and the central unit 58 for identification purposes. In the event that the proper activation signal is not transmitted with each communication, it may be ignored. The activation may be revoked, numeral 38, at a later time if the authorization is withdrawn or for other reasons. Upon revocation 38, the signals transmitted by the medical monitoring device 54 are not acted upon, and the patient and/or issuing authority is notified and requested to return the medical monitoring device 54. As an alternative to revocation 38, the activation signal of step 34 may include a maximum time limit for which activation is authorized, so that a further authorization is required to extend the period of authorized use.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for controlling access to medical monitoring device service, comprising the steps of:
   providing a medical monitoring device system having communications access to a central unit;
   inputting a set of identification data elements into the medical monitoring device system;
   the medical monitoring device system establishing a communication link with the central unit and communicating the set of identification data elements to the central unit;
   the medical monitoring device system and the central unit cooperatively determining whether the medical monitoring device system may be activated for rendering medical monitoring device service, the step of determining including the steps of
      evaluating the set of identification data elements as to whether they meet a set of basic structural requirements, and
      obtaining authorization from a third-party source; and, in the event that the identification data elements meet the set of basic structural requirements and authorization is obtained,
   issuing an activation signal to the medical monitoring device system over the communication link.

2. The method of claim 1, wherein the medical monitoring device system comprises a patient-portable unit.

3. The method of claim 1, including an additional step, after the step of issuing an activation signal, of
   a patient-portable unit subsequently communicating with the central unit, and
   the patient-portable unit including the activation signal and the subsequent communications with the central unit.

4. The method of claim 1, wherein the medical monitoring device system comprises a patient-portable unit and a base station in communication with the patient-portable unit.

5. The method of claim 1, wherein the communication link is a land-line.

6. The method of claim 1, wherein the communication link is a wireless link.

7. The method of claim 1, wherein the set of identification data elements is selected from the group consisting of a patient name, a patient address, a patient social security number, a patient sex, and an identification of a third-party source.

8. The method of claim 1, wherein the steps of evaluating and obtaining are performed by the central unit.

9. The method of claim 1, wherein the steps of evaluating and obtaining are performed automatically.

10. The method of claim 1, wherein the step of inputting includes the step of
    the medical monitoring device system locally performing a preliminary evaluation of the set of identification data elements as to whether they meet a set of format requirements, and
    the medical monitoring device system providing an input diagnostic message in the event that the step of performing a preliminary evaluation determines that the set of identification data elements does not meet the set of format requirements.

11. The method of claim 1, wherein the third-party source is selected from the group consisting of an insurance company, the social security administration, and a credit-granting company.

12. A method for controlling access to medical monitoring device service to monitor a patient, comprising the steps of:

provabling a medical monitoring device system having communications access to a central unit, wherein the medical monitoring device system comprises a patient-portable unit and a base station in communication with the patient-portable unit;

inputting a set of identification data elements into the medical monitoring device system;

the medical monitoring device system establishing a communication link with the central unit and communicating the set of identification data elements to the central unit;

the central unit determining whether the medical monitoring device system may be activated for rendering medical monitoring device service, the step of determining including the steps of automatically evaluating the set of identification data elements as to whether they meet a set of basic structural requirements, and automatically obtaining financial authorization from a third-party financial source; in the event that the identification data elements meet the set of basic structural requirements and financial authorization is obtained, the central unit issuing an activation signal to the medical monitoring device system over the communication link;

the patient-portable unit activating responsive to the activation signal; and thereafter the patient-portable unit providing medical monitoring device service to the patient.

13. The method of claim 12, including an additional step, after the step of the central unit issuing an activation signal, of the patient-portable unit subsequently communicating with the central unit, and the patient-portable unit including the activation signal in the subsequent communications with the central unit.

14. The method of claim 12, wherein the communication link is a land-line.

15. The method of claim 12, wherein the communication link is a wireless link.

16. The method of claim 12, wherein the set of identification data elements is selected from the group consisting of a patient name, a patient address, a patient social security number, a patient sex, and an identification of the third-party financial source.

17. The method of claim 12, wherein the step of inputting includes the step of the medical monitoring device system locally performing a preliminary evaluation of the set of identification data elements as to whether they meet a set of format requirements, and the medical monitoring device system providing an input diagnostic message in the event that the step of performing a preliminary evaluation determines that the set of identification data elements does not meet the set of format requirements.

18. The method of claim 12, wherein the third-party financial source is selected from the group consisting of an insurance company, the social security administration, and a credit-granting company.

19. A method for controlling access to medical monitoring device service, comprising the steps of:

providing a medical monitoring device system having communications access to a central unit;

inputting a set of identification data elements into the medical monitoring device system;

the medical monitoring device system establishing a communication link with the central unit and communicating the set of identification data elements to the central unit;

the medical monitoring device system and the central unit cooperatively determining whether the medical monitoring device system may be activated for rendering medical monitoring device service, the step of determining including the steps of automatically evaluating the set of identification data elements as to whether they meet a set of basic structural requirements, and automatically obtaining third-party authorization from a third-party source; and, in the event that the identification data elements meet the set of basic structural requirements and third-party authorization is obtained, issuing an activation signal to the medical monitoring device system over the communication link.

\* \* \* \* \*